US008198503B2

(12) United States Patent
Urankar et al.

(10) Patent No.: US 8,198,503 B2
(45) Date of Patent: Jun. 12, 2012

(54) DISPOSABLE ABSORBENT ARTICLES COMPRISING ODOR CONTROLLING MATERIALS

(75) Inventors: Edward Joseph Urankar, Mason, OH (US); Sharon Anne Keegan, Lawrenceburg, IN (US); Randall Alan Watson, Loveland, OH (US); Gregory Scot Miracle, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 573 days.

(21) Appl. No.: 12/272,967

(22) Filed: Nov. 18, 2008

(65) Prior Publication Data

US 2009/0148686 A1   Jun. 11, 2009

Related U.S. Application Data

(60) Provisional application No. 60/989,071, filed on Nov. 19, 2007.

(51) Int. Cl.
*A61F 13/15* (2006.01)
(52) U.S. Cl. .................. 604/359; 604/360; 604/367
(58) Field of Classification Search .................. 604/359, 604/360, 367
See application file for complete search history.

(56) References Cited

U.S. PATENT DOCUMENTS

| | | | |
|---|---|---|---|
| 3,340,875 A | 9/1967 | Dudley et al. | |
| 3,563,243 A | 2/1971 | Lindquist | |
| 3,812,044 A | 5/1974 | Connor et al. | |
| 3,986,972 A | 10/1976 | Loffelman et al. | |
| 4,259,383 A * | 3/1981 | Eggensperger et al. | 428/72 |
| 4,289,513 A | 9/1981 | Brownhill et al. | |
| 4,356,190 A | 10/1982 | Kraskin | |
| 4,363,322 A | 12/1982 | Andersson | |
| 4,412,934 A | 11/1983 | Chung et al. | |
| 4,430,243 A | 2/1984 | Bragg | |
| 4,483,781 A | 11/1984 | Hartman | |
| 4,486,327 A | 12/1984 | Murphy et al. | |
| 4,610,678 A | 9/1986 | Weisman et al. | |
| 4,634,551 A | 1/1987 | Burns et al. | |
| 4,673,402 A | 6/1987 | Weisman et al. | |
| 4,728,455 A | 3/1988 | Rerek | |
| 4,740,520 A | 4/1988 | Hallenbach et al. | |
| 4,810,410 A | 3/1989 | Diakun et al. | |
| 4,834,735 A | 5/1989 | Alemany et al. | |
| 4,888,231 A | 12/1989 | Angstadt | |

(Continued)

FOREIGN PATENT DOCUMENTS

EP   0133354 A1   2/1985

(Continued)

OTHER PUBLICATIONS

International Search Report and Written Opinion, PCT/IB2008/054864, mailed Nov. 19, 2008, 13 pages. W.L. Jolly, "The Preparation of Chloropenta-Ammine Cobalt (III) Chloride, Nitropentaamminecobalt (III) Chloride, and Nitritopentaammine-Cobalt (III) Chloride", *Prentice-Hall*, pp. 461-463 (1970).
Jackman et al., "Synthesis of Transition-Metal Carboxylato Complexes", *Inorganic Chemistry*, vol. 18, No. 6, pp. 1497-1502 and vol. 18, No. 7, pp. 2023-2025 (1979).

(Continued)

*Primary Examiner* — Jacqueline F. Stephens
(74) *Attorney, Agent, or Firm* — Richard L. Alexander; Amy M. Foust; Abbey A. Lopez

(57) ABSTRACT

The present inventions relates to a disposable absorbent articles, including diapers and sanitary napkins, comprising a bleach activator system for controlling odors associated with bodily fluids. The bleach activator system may comprise a peroxygen bleach compound (including a source of hydrogen peroxide) and a bleach activator compound capable of generating a peroxyacid in-situ within the absorbent article.

20 Claims, 3 Drawing Sheets

U.S. PATENT DOCUMENTS

| | | |
|---|---|---|
| 4,915,854 A | 4/1990 | Mao et al. |
| 4,966,723 A | 10/1990 | Hodge et al. |
| 5,004,558 A | 4/1991 | Dyroff et al. |
| 5,114,606 A | 5/1992 | Van Vliet et al. |
| 5,114,611 A | 5/1992 | Van Kralingen et al. |
| 5,130,045 A | 7/1992 | Mitchell et al. |
| 5,132,431 A | 7/1992 | Fuchs et al. |
| 5,147,345 A | 9/1992 | Young et al. |
| 5,153,161 A | 10/1992 | Kerschner et al. |
| 5,194,416 A | 3/1993 | Jureller et al. |
| 5,227,084 A | 7/1993 | Martens et al. |
| 5,234,423 A | 8/1993 | Alemany et al. |
| 5,244,594 A | 9/1993 | Favre et al. |
| 5,246,612 A | 9/1993 | Van Dijk et al. |
| 5,246,620 A | 9/1993 | Gethoffer et al. |
| 5,246,621 A | 9/1993 | Favre et al. |
| 5,256,779 A | 10/1993 | Kerschner et al. |
| 5,260,345 A | 11/1993 | Desmarais et al. |
| 5,274,147 A | 12/1993 | Kerschner et al. |
| 5,279,757 A | 1/1994 | Gethoffer et al. |
| 5,280,117 A | 1/1994 | Kerschner et al. |
| 5,284,944 A | 2/1994 | Madison et al. |
| 5,310,934 A | 5/1994 | Cavallotti et al. |
| 5,360,569 A | 11/1994 | Madison et al. |
| 5,370,826 A | 12/1994 | Madison et al. |
| 5,405,412 A | 4/1995 | Willey et al. |
| 5,405,413 A | 4/1995 | Willey et al. |
| 5,460,747 A | 10/1995 | Gosselink et al. |
| 5,478,357 A | 12/1995 | Madison et al. |
| 5,482,515 A | 1/1996 | Madison et al. |
| 5,487,818 A | 1/1996 | Cavallotti et al. |
| 5,503,639 A | 4/1996 | Willey et al. |
| 5,523,434 A | 6/1996 | Burns et al. |
| 5,542,066 A | 7/1996 | Mattson et al. |
| 5,550,256 A | 8/1996 | Madison et al. |
| 5,554,297 A | 9/1996 | Tanii |
| 5,562,646 A | 10/1996 | Goldman et al. |
| 5,576,282 A | 11/1996 | Miracle et al. |
| 5,578,136 A | 11/1996 | Taylor et al. |
| 5,584,888 A | 12/1996 | Miracle et al. |
| 5,595,967 A | 1/1997 | Miracle et al. |
| 5,597,936 A | 1/1997 | Perkins et al. |
| 5,599,335 A | 2/1997 | Goldman et al. |
| 5,669,894 A | 9/1997 | Goldman et al. |
| 5,686,014 A | 11/1997 | Baillely et al. |
| 5,686,015 A | 11/1997 | Willey et al. |
| 5,695,679 A | 12/1997 | Christie et al. |
| 5,698,504 A | 12/1997 | Christie et al. |
| 5,703,030 A | 12/1997 | Perkins et al. |
| 5,718,614 A | 2/1998 | Armond et al. |
| 5,739,327 A | 4/1998 | Arbogast et al. |
| 5,741,437 A | 4/1998 | Arbogast et al. |
| 5,877,315 A | 3/1999 | Deline et al. |
| 5,958,289 A | 9/1999 | Arbogast et al. |
| 5,998,350 A | 12/1999 | Burns et al. |
| 6,017,464 A | 1/2000 | Deline |
| 6,025,186 A | 2/2000 | Kirk et al. |
| 6,063,750 A | 5/2000 | Loffler et al. |
| 6,133,216 A | 10/2000 | Loffler et al. |
| 6,140,294 A | 10/2000 | Delroisse et al. |
| 6,287,580 B1 | 9/2001 | Gott et al. |
| 6,302,921 B1 | 10/2001 | Delroisse et al. |
| 6,417,300 B1 | 7/2002 | Joubert et al. |
| 6,528,014 B1 | 3/2003 | Parkhurst et al. |
| 6,627,786 B2 | 9/2003 | Roe et al. |
| 6,649,805 B1 | 11/2003 | Carlucci et al. |
| 6,730,819 B1 | 5/2004 | Pesce |
| 6,790,798 B1 | 9/2004 | Suzuki et al. |
| 6,887,496 B2 | 5/2005 | Koenig et al. |
| 7,141,518 B2 | 11/2006 | MacDonald et al. |
| 7,147,822 B2 | 12/2006 | Parkhurst et al. |
| 7,163,737 B2 * | 1/2007 | De Almeida et al. ......... 428/323 |
| 7,235,263 B2 | 6/2007 | Koenig et al. |
| 2003/0082082 A1 | 5/2003 | Parkhurst et al. |
| 2004/0097895 A1 | 5/2004 | Busam et al. |
| 2004/0158212 A1 | 8/2004 | Ponomarenko et al. |
| 2004/0162538 A1 | 8/2004 | Mueller et al. |
| 2005/0095942 A1 | 5/2005 | Mueller et al. |
| 2005/0171499 A1 | 8/2005 | Nigam et al. |
| 2005/0273071 A1 | 12/2005 | McKiernan et al. |
| 2006/0292091 A1 | 12/2006 | Prosise |
| 2007/0191806 A1 | 8/2007 | Mueller et al. |
| 2007/0264356 A1 * | 11/2007 | Ames ........................... 424/616 |

FOREIGN PATENT DOCUMENTS

| | | |
|---|---|---|
| EP | 510619 A1 | 10/1992 |
| EP | 544490 A1 | 6/1993 |
| EP | 549271 A1 | 6/1993 |
| EP | 549272 A1 | 6/1993 |
| EP | 555440 B1 | 8/1993 |
| EP | 604919 A1 | 7/1994 |
| EP | 0658350 A1 | 6/1995 |
| EP | 790244 A1 | 8/1997 |
| EP | 1017773 B1 | 7/2000 |
| EP | 1034799 A1 | 9/2000 |
| EP | 1034800 A1 | 9/2000 |
| EP | 1034801 A1 | 9/2000 |
| EP | 1034802 A1 | 9/2000 |
| EP | 1034804 A1 | 9/2000 |
| EP | 1034805 A1 | 9/2000 |
| EP | 1159013 A1 | 9/2000 |
| EP | 1017776 B1 | 7/2002 |
| EP | 1019103 B1 | 7/2002 |
| EP | 775127 B1 | 9/2003 |
| EP | 1463537 B1 | 1/2007 |
| EP | 1159014 B1 | 4/2007 |
| GB | 2377890 A | 1/2003 |
| WO | WO 81/01643 | 6/1981 |
| WO | WO 89/02698 | 4/1989 |
| WO | WO 91/11977 | 8/1991 |
| WO | WO 91/12029 | 8/1991 |
| WO | WO 91/12030 | 8/1991 |
| WO | WO 94/25077 | 11/1994 |
| WO | WO 94/26317 | 11/1994 |
| WO | WO 94/28102 A1 | 12/1994 |
| WO | WO 95/02330 A1 | 1/1995 |
| WO | WO 95/13351 A1 | 5/1995 |
| WO | WO 95/13352 A1 | 5/1995 |
| WO | WO 95/13353 A1 | 5/1995 |
| WO | WO 96/40661 A1 | 12/1996 |
| WO | WO 99/08726 A1 | 2/1999 |
| WO | WO 99/14296 A1 | 3/1999 |
| WO | WO 00/51651 A1 | 9/2000 |
| WO | WO 00/51652 A1 | 9/2000 |
| WO | WO 00/51653 A1 | 9/2000 |
| WO | WO 00/51654 A1 | 9/2000 |
| WO | WO 00/51655 A1 | 9/2000 |
| WO | WO 00/51656 A1 | 9/2000 |
| WO | WO 00/51657 A1 | 9/2000 |
| WO | WO 02/22970 A1 | 3/2002 |
| WO | WO 03/053481 A1 | 7/2003 |
| WO | WO 2005/006862 A2 | 1/2005 |
| WO | WO 2005/080542 A1 | 9/2005 |
| WO | WO 2005/120594 A1 | 12/2005 |
| WO | WO 2007/127641 A1 | 11/2007 |
| WO | WO 2008/058565 A1 | 5/2008 |

OTHER PUBLICATIONS

Wierenga et al., "Synthesis and Characterization of Cobalt (III) Nicotinic Acid Complexes", *Inorg. Chem.*, 21, pp. 2881-2885 (1982).

Basolo et al., "Mechanism of Substitution Reactions in Complex Ions. I. Kinetics of the Aquation and Hydrolysis of Some C-Substituted Acetatopentamminecobalt (III) Ions", *Journal of Physical Chemistry*, vol. 56, pp. 22-25 (1952).

Kirk Othmer's Encyclopedia of Chemical Technology, 4$^{th}$ Ed. (1992, John Wiley & Sons), vol. 4, pp. 271-300 Bleaching Agents (Survey).

Kirk Othmer's Encyclopedia of Chemical Technology, (1982, John Wiley & Sons), vol. 17, pp. 27-90.

M. L. Tobe, "Base Hydrolysis of Transition-Metal Complexes", Adv. Inorg. Bioinorg. Mech., (1983), 2, pp. 1-94.

Williams, et al., "Coordination Complexes of Cobalt", J. Chem Ed. (1989), 66 (12), 1043-45.

* cited by examiner

DISPOSABLE ABSORBENT ARTICLES COMPRISING ODOR CONTROLLING MATERIALS

CROSS REFERENCE TO RELATED APPLICATION

This application claims the benefit of U.S. Provisional Application No. 60/989,071, filed Nov. 19, 2007, the substance of which is incorporated herein by reference.

FIELD OF INVENTION

The present disclosure generally relates to bleach activator systems and methods for incorporating such systems into disposable absorbent articles.

BACKGROUND OF THE INVENTION

Absorbent articles, such as disposable diapers, sanitary napkins, pantiliners, incontinence pads, tampons, and the like are typically utilized for absorbing body fluids such as urine, feces, vaginal fluids, and menses. Upon absorbing these fluids, the absorbent articles can be found to contain a number of volatile chemical compounds that include fatty acids (e.g., isovaleric acid), sulfur containing compounds (e.g., mercaptans and sulfides), ammonia, amines (e.g., triethylamine), ketones (e.g., 4-heptanone), alcohols, and aldehydes (decanal) which contribute to the unpleasant odors which can be released from these products during wear or upon disposal. The compounds may be present in the bodily fluids or may develop over time by chemical reaction and/or fluid degradation mechanisms once the fluid has been absorbed into the absorbent article. In addition, once the bodily fluids have been absorbed into the absorbent article, they usually come in contact with microorganisms and/or enzymes that can also generate malodorous by-products as a result of degradation mechanisms such as putrefactive degradation, acid degradation, protein degradation, fat degradation, and the like. These odors can lead to unpleasant experiences for the wearer of the absorbent article and caregiver alike and can make the discreet use and/or disposal of the absorbent articles difficult.

Various odor control materials, agents, techniques, and systems have been disclosed in the art to combat some of the unpleasant odors referred to above, including masking (i.e., covering the odor with a perfume), absorbing the odor already present in the bodily fluids and those generated after degradation, or preventing the formation of the odor. Most of the focus in the prior art is on odor adsorption technology. Examples of these types of compounds include activated carbons, clays, zeolites, silicates, absorbing gelling materials, starches, cyclodextrin, ion exchange resins, and various mixtures thereof (see, for example, EP-A-348 978, EP-A-510 619, WO 91/12029, WO 91/11977, WO 89/02698, and/or WO 91/12030). Odor control systems of the prior art are one-dimensional. For instance, mechanisms where the malodorous compounds and their precursors are physically adsorbed by odor control agents, and thereby hindered from exiting the articles, are not completely effective as the formation of the odor itself is not prevented, and thus odor detection is not completely avoided. Additionally, fragrances are typically used within absorbent articles to enhance the user experience with the product (e.g., fresh-scent bursts). These fragrances are often added at low levels and provide only a marginal odor control benefit over the entire use cycle of the product. Further, adsorbent technologies (e.g., activated carbon) are often not compatible with fragrances because they can be adsorbed and removed from the absorbent article by the adsorbent technologies of the prior art. Thus, although prior art odor control materials provide some control of odors associated with bodily fluids, there still exists a need to provide multidimensional and compatible odor control agents and systems.

It is an object of the present invention to provide effective odor control over a wider range of malodorous compounds and to provide that odor control benefit in instances when fragrance may be present in the absorbent article. Additionally, it is an object of the present invention to provide disposable absorbent articles which provide multiple mechanisms for combating odor, including, but not limited to, reacting with the odor causing molecules and preventing the formation of malodors.

It has been found that the objects of the present inventions are accomplished by using a bleach activator system. An embodiment of a bleach activator system of the present invention is a combination of sodium percarbonate and sodium nonanoyloxybenzenesulfonate (NOBS), which is capable of generating a peroxyacid in-situ within a disposable absorbent article to control malodor.

The laundry industry developed a class of materials known as "bleach activators". Bleach activators, typically perhydrolyzable acyl compounds having a leaving group such as oxybenzenesulfonate (OBS), react with the active oxygen group, typically hydrogen peroxide or its anion, to form a more effective peroxyacid oxidant. In the laundry context, it is the peroxyacid compound which then oxidizes the stained or soiled substrate. While hydrogen peroxide at modest concentrations can bleach effectively at temperatures of about 60° C. and above, use of bleach activators enables effective bleaching at significantly lower temperatures. Numerous substances have been disclosed in the art as effective bleach activators. One widely-used bleach activator is tetraacetyl ethylene diamine (TAED). Another type of activator, such as nonanoyloxybenzenesulfonate (NOBS) and other activators which generally comprise long chain alkyl moieties, yields a peracid that is hydrophobic in nature and provides excellent performance on dingy stains Surprisingly, bleach activator systems that generate in-situ peroxyacids can be used in absorbent articles for significantly decreasing bodily odor. These results are evident when absorbent articles comprising a bleach activator system of the present system are compared to the same absorbent article not having the bleach activator system. While not wishing to be bound to theory, it is speculated that the peroxyacids formed in-situ according to the present invention have a dual odor control mechanism: first, they prevent the generation of odor in the absorbent article by blocking enzymatic and/or microbial activity; and second, they combat the odors already present in the absorbent article by oxidizing them into non-odiferous molecules.

In contrast to the use of pre-formed peroxyacids of the prior art, bleach activator systems of the present invention generate the reactive odor control agents only when they are most needed in the absorbent article (i.e., at the time of collection of the waste bodily fluid (e.g., urine, menstrual fluid, and runny bowel exudates)). This is advantageous with reactive materials such as peroxyacids because it lessens the possibility that the material will prematurely react with other materials found in the absorbent article prior to use and it increases the likelihood that the reactive odor control agents are available when needed (e.g., post urine insult). In this way, bleach activator systems of the present invention comprise precursor peroxyacids that are activatable.

Additionally, in-situ generation of peroxyacids via bleach activator systems described herein offers the distinct advantage that they can be used in the presence of a wide variety of fragrance materials. Because formation of the peroxyacid is generated by the bleach activator system upon contact with aqueous media, significant reductions in the concentration of the perfume raw materials prior to insult (due to incompatibility with the peroxyacid or adsorption on the surface of the odor control media) is avoided and enables the fragrance to enhance the overall product experience, especially upon initial opening of the product packaging.

An additional advantage of the in-situ generated peroxyacids of the present invention is that the generation of malodorous smelling by-products like chlorine derivatives and ammonium derivatives is avoided when they come into contact with bodily fluids. In contrast to the in-situ generated peroxyacids of the present invention, oxidants like persulphate, periodate, percarbonate, and/or perborate oxidize the chlorides usually present in bodily fluids into chlorine derivatives that are not acceptable to the consumer from an odor point of view. Also in contrast to the in-situ generated peroxyacids of the present invention, oxidants like urea peroxides, calcium peroxides, strontium peroxides and/or barium peroxides (i.e., compounds having an alkaline pH) promote the formation of malodorous ammonia derivatives (i.e., one of the by-products of proteins degradation occurring in the bodily fluids when they come into contact with it).

SUMMARY OF THE INVENTION

The present invention relates to an absorbent article comprising a topsheet, a backsheet, an absorbent core between the topsheet and backsheet, and an odor control system. The odor control system may comprise a bleach activator system. The bleach activator system may comprise a peroxygen bleaching compound and a bleach activator capable of reacting with the peroxygen bleaching compound to form a peracid. The peroxygen bleaching compound may be a source of hydrogen peroxide.

DETAILED DESCRIPTION OF THE INVENTION

Figure 1:
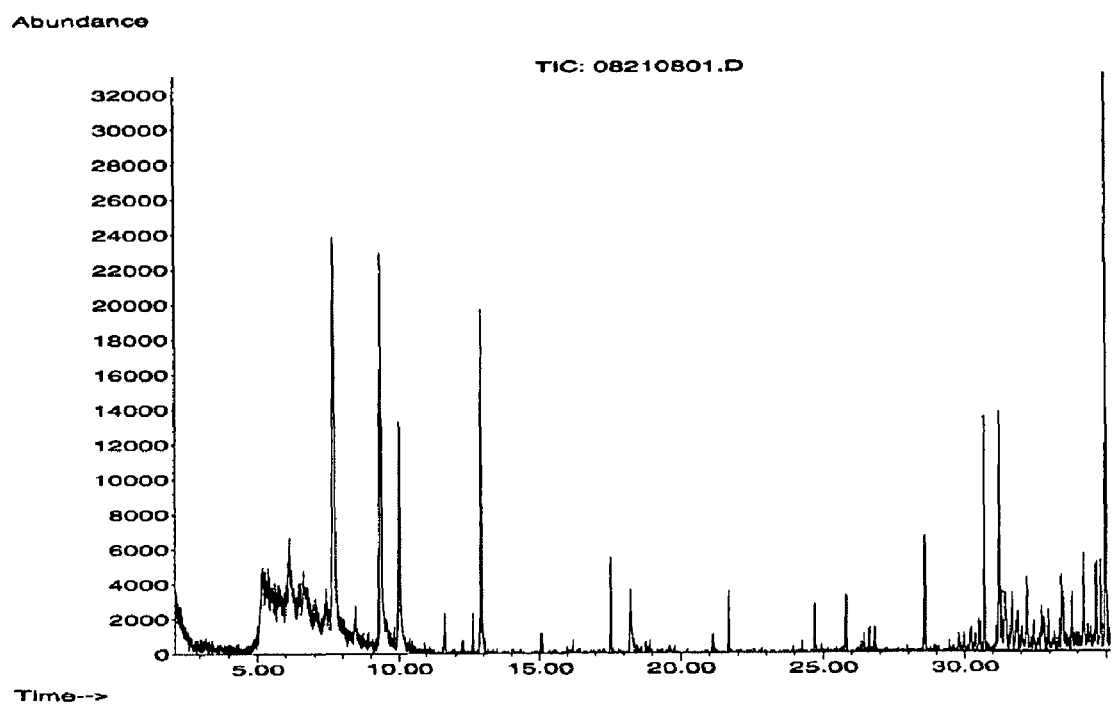
FIG. 1 is an example Headspace GC/MS analysis of an aged urine loaded control (blank) diaper.
Figure 2:
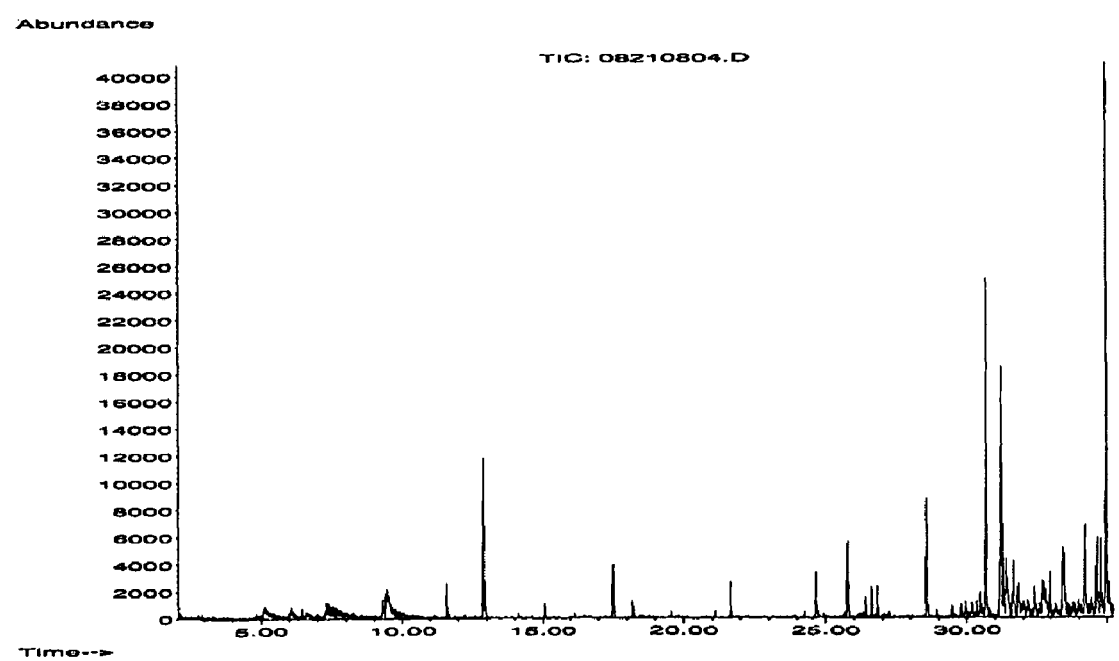
FIG. 2 is an example Headspace GC/MS analysis of an aged urine loaded diaper comprising sodium percarbonate alone (See Example 5).
Figure 3:
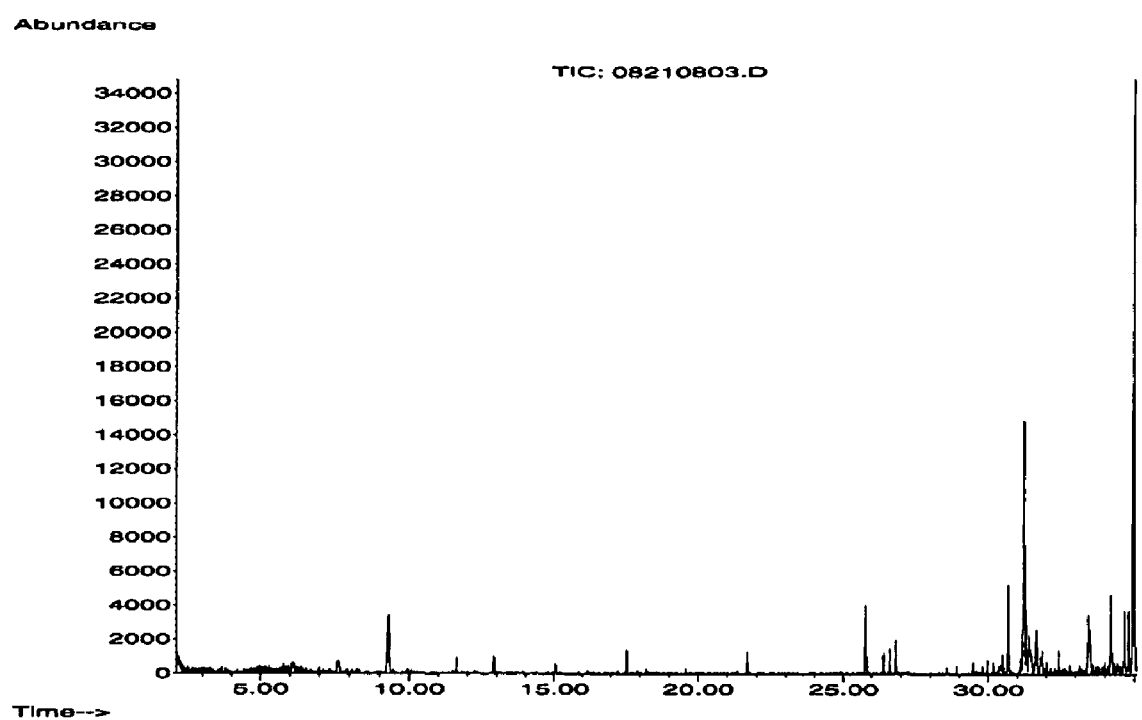
FIG. 3 is an example Headspace GC/MS analysis of an aged urine loaded diaper comprising a multiple particle bleach activator odor control system (See Example 4).

The disposable absorbent articles according to the present invention may comprise an odor control system. The odor control system may comprise a bleach activator system. The bleach activator system may comprise a peroxygen bleaching compound and a bleach activator described herein after.

The Peroxygen Bleaching Compound

The peroxygen bleaching compounds of the present invention include those capable of yielding hydrogen peroxide in aqueous liquor. Hydrogen peroxide sources are described in detail in Kirk Othmer's Encyclopedia of Chemical Technology, 4th Ed (1992, John Wiley & Sons), Vol. 4, pp. 271-300 "Bleaching Agents (Survey)," and include the various forms of sodium perborate and sodium percarbonate, including various coated and modified forms.

The sources of hydrogen peroxide of the present invention may include any convenient source, including hydrogen peroxide itself. For example, perborate, e.g., sodium perborate (any hydrate including the mono- or tetra-hydrate), sodium carbonate peroxyhydrate or equivalent percarbonate salts, sodium pyrophosphate peroxyhydrate, urea peroxyhydrate, or sodium peroxide may be used. Also useful are sources of available oxygen such as persulfate bleach (e.g., OXONE, manufactured by DuPont). Sodium perborate monohydrate and sodium percarbonate are further examples. Other useful sources of hydrogen peroxide include stable complexes of polyvinylpyrrolidone with hydrogen peroxide (as disclosed in U.S. Patent App. No. 2006/0292091 and available from International Specialty Products, N.J. under the tradename Peroxydone) and stable crystalline complexes of carbohydrate and hydrogen peroxide (as disclosed in U.S. Pat. No. 6,887,496. Mixtures of any hydrogen peroxide sources can also be used.

A percarbonate bleach may comprise dry particles having an average particle size in the range from about 500 micrometers to about 1,000 micrometers, not more than about 10% by weight of the particles being smaller than about 200 micrometers and not more than about 10% by weight of the particles being larger than about 1,250 micrometers. Optionally, the percarbonate can be coated with a silicate, borate or water-soluble surfactants. Sodium Percarbonate, available from OCI Chemical Corp, Decatur, Ala. under the tradename Provox C or Kemira Kemi AB, Sweden under the tradename ECOX-C, can be in uncoated or coated form, and can be used in the present invention.

The Bleach Activator

The peroxygen bleach compound may be formulated with a bleach activator. The bleach activator may be considered a "peracid precursor." The bleach activator may be present within the absorbent article at levels from about 0.001 g, from about 0.005 g, from about 0.01 g to about 0.05 g, to about 0.2 g, to about 1.0 g per absorbent article. The bleach activator may include any compound, which when used in conjunction with a hydrogen peroxide source, results in the in-situ production of a peracid corresponding to the bleach activator. Examples of bleach activators are disclosed in U.S. Pat. Nos. 5,576,282; 4,915,854; and 4,412,934. U.S. Pat. No. 4,634,551 also discloses peroxygen bleaching compounds and bleach activators of the present invention.

Bleach activators may include tetraacetyl ethylene diamine (TAED), benzoylcaprolactam (BzCL), 4-nitrobenzoylcaprolactam, 3-chlorobenzoylcaprolactam, benzoyloxybenzenesulphonate (BOBS), nonanoyloxybenzenesulphonate (NOBS), phenyl benzoate (PhBz), decanoyloxybenzenesulphonate ($C_{10}$-OBS), benzoylvalerolactam (BZVL), octanoyloxybenzenesulphonate ($C_8$-OBS), perhydrolyzable esters and mixtures thereof, and benzoylcaprolactam and benzoylvalerolactam. Bleach activators that have an OBS or VL leaving group may be used in the present invention.

Hydrophobic bleach activators may be used and may include, nonanoyloxybenzenesulphonate (NOBS), 4-[N-(nonaoyl) amino hexanoyloxy]-benzene sulfonate sodium salt (NACA-OBS), an example of which is described in U.S. Pat. No. 5,523,434, dodecanoyloxybenzenesulphonate (LOBS or $C_{12}$-OBS), 10-undecenoyloxybenzenesulfonate (UDOBS or $C_{11}$-OBS with unsaturation in the 10 position), and decanoyloxybenzoic acid (DOBA).

Bleach activators of the present invention are also described in U.S. Pat. Nos. 5,698,504; 5,695,679; 5,686,401;

5,686,014; 5,405,412; 5,405,413; 5,130,045; 4,412,934; and U.S. Ser. Nos. 08/709,072; and 08/064,564.

The mole ratio of hydrogen peroxide (neat or as delivered from the peroxygen source) to bleach activator in the present invention may range from at about 100:1 to 1:1; from about 80:1 to 5:1, and from about 70:1 to about 20:1.

Quaternary substituted bleach activators (QSBAs) and quaternary substituted peracids (QSPs) may also be used. QSBA structures are further described in U.S. Pat. Nos. 5,686,015; 5,654,421; 5,460,747; 5,584,888; and 5,578,136.

Also, bleach activators of the present invention may include ones that are amide-substituted as described in U.S. Pat. Nos. 5,698,504; 5,695,679; and 5,686,014. Examples of such bleach activators include: (6-octanamidocaproyl)oxybenzenesulfonate, (6-nonanamidocaproyl)oxybenzenesulfonate, (6-decanamidocaproyl)oxybenzenesulfonate, and mixtures thereof.

Other useful bleach activators that may be used in the present invention are disclosed in U.S. Pat. Nos. 5,698,504; 5,695,679; 5,686,014; and 4,966,723. Included in one or more of these patents is benzoxazin-type activators, such as a $C_6H_4$ ring to which is fused in the 1,2-positions a moiety —C(O)OC($R^1$)=N—.

Nitriles, such as acetonitriles and/or ammonium nitriles and other quaternary nitrogen containing nitriles, are another class of bleach activators that may be useful in the present invention. Nitrile bleach activators are described in U.S. Pat. Nos. 6,133,216; 3,986,972; 6,063,750; 6,017,464; 5,958,289; 5,877,315; 5,741,437; 5,739,327; and 5,004,558, as well as EP Nos. 790 244; 775 127; 1 017 773; 1 017 776, and, finally as described in WO Nos. 99/14302; 99/14296; and WO96/40661.

Acyl lactam bleach activators, as described in U.S. Pat. Nos. 5,698,504; 5,695,679; and 5,686,014 may be used in the present invention. For example, acyl caprolactams (see WO 94-28102) and acyl valerolactams (see U.S. Pat. No. 5,503,639) may be used.

Further, sodium nonanoyloxybenzenesulfonate, available from Future Fuel Company, Batesville, Ark. may be used as a bleach activator in the present invention. The absorbent article of the present invention may comprise a single class of bleach activator compounds or it may comprise a combination of bleach activator compounds.

Optional Agents

The absorbent articles of the present invention may further comprise, in addition to the bleach activator systems described herein, other conventional bleaching agents and dispersants, or mixtures thereof.

Organic Peroxides may be used in the present invention, including Diacyl Peroxides, which are illustrated in Kirk Othmer, Encyclopedia of Chemical Technology, Vol. 17, John Wiley and Sons, 1982 at pages 27-90 and especially at pages 63-72.

Metal-containing Bleach Catalysts may be used in the present invention, including manganese and cobalt-containing bleach catalysts. One type of metal-containing bleach catalyst is a catalyst system comprising a transition metal cation of defined bleach catalytic activity, such as copper, iron, titanium, ruthenium tungsten, molybdenum, or manganese cations, an auxiliary metal cation having little or no bleach catalytic activity, such as zinc or aluminum cations, and a sequestrate having defined stability constants for the catalytic and auxiliary metal cations, ethylenediaminetetraacetic acid, ethylenediaminetetra (methylenephosphonic acid) and water-soluble salts thereof. Such catalysts are disclosed in U.S. Pat. No. 4,430,243.

Manganese Metal Complexes may be used in the present invention, including the manganese-based catalysts disclosed in U.S. Pat. Nos. 5,576,282; 5,246,621; 5,244,594; 5,194,416; and 5,114,606; and European Pat. App. Pub. Nos. 549,271 A1; 549,272 A1; 544,440 A2; and 544,490 A1. Examples of these catalysts include $Mn^{IV}_2$(u-O)$_3$(1,4,7-trimethyl-1,4,7-triazacyclononane)$_2$(PF$_6$)$_2$, $Mn^{III}_2$(u-O)$_1$(u-OAc)$_2$(1,4,7-trimethyl-1,4,7-triazacyclononane)$_2$(ClO$_4$)$_2$, $Mn^{IV}_4$(u-O)$_6$(1,4,7-triazacyclononane)$_4$(ClO$_4$)$_4$, $Mn^{III}Mn^{IV}_4$(u-O)$_1$(u-OAc)$_2$-(1,4,7-trimethyl-1,4,7-triazacyclononane)$_2$(ClO$_4$)$_3$, $Mn^{IV}$(1,4,7-trimethyl-1,4,7-triazacyclononane)-(OCH$_3$)$_3$(PF$_6$), and mixtures thereof. Other metal-based bleach catalysts may include those disclosed in U.S. Pat. Nos. 4,430,243 and 5,114,611. The use of manganese with various complex ligands to enhance bleaching is also reported in U.S. Pat. Nos. 4,728,455; 5,284,944; 5,246,612; 5,256,779; 5,280,117; 5,274,147; 5,153,161; and 5,227,084.

Cobalt Metal Complexes may be used in the present invention, including those describe in U.S. Pat. Nos. 5,597,936; 5,595,967; and 5,703,030; and in M. L. To be, "Base Hydrolysis of Transition-Metal Complexes", Adv. Inorg. Bioinorg. Mech., (1983), 2, pages 1-94. Examples include cobalt pentaamine acetate salts having the formula [Co(NH$_3$)$_5$OAc] T$_y$, wherein "OAc" represents an acetate moiety and "T$_y$" is an anion, and especially cobalt pentaamine acetate chloride, [Co(NH$_3$)$_5$OAc]Cl$_2$; as well as [Co(NH$_3$)$_5$OAc](OAc)$_2$; [Co(NH$_3$)$_5$OAc](PF$_6$)$_2$; [Co(NH$_3$)$_5$OAc] (SO$_4$); [Co(NH$_3$)$_5$OAc] (BF$_4$)$_2$; and [Co(NH$_3$)$_5$OAc] (NO$_3$)$_2$ (herein "PAC").

Iron Metal Complexes may be used in the present invention, including those describe in U.S. Pat. Nos. 6,302,921; 6,287,580; 6,140,294; 5,597,936; 5,595,967; 4,810,410 and 5,703,030; and in J. Chem. Ed. (1989), 66 (12), 1043-45; The Synthesis and Characterization of Inorganic Compounds, W. L. Jolly (Prentice-Hall; 1970), pp. 461-3; Inorg. Chem., 18, 1497-1502 (1979); Inorg. Chem., 21, 2881-2885 (1982); Inorg. Chem., 18, 2023-2025 (1979); Inorg. Synthesis, 173-176 (1960); and Journal of Physical Chemistry, 56, 22-25 (1952). Transition Metal Complexes of Macropolycyclic Rigid may be used in the present invention. Transition-metal bleach catalysts of Macrocyclic Rigid Ligands which are suitable for use in the invention compositions may include the following:

Dichloro-5,12-dimethyl-1,5,8,12-tetraazabicyclo[6.6.2] hexadecane Manganese(II)
Dichloro-5,12-diethyl-1,5,8,12-tetraazabicyclo[6.6.2]hexadecane Manganese(II)
Diaquo-5,12-dimethyl-1,5,8,12-tetraazabicyclo[6.6.2]hexadecane Manganese(II) Hexafluorophosphate
Diaquo-5,12-diethyl-1,5,8,12-tetraazabicyclo[6.6.2]hexadecane Manganese(II) Hexafluorophosphate
Aquo-hydroxy-5,12-dimethyl-1,5,8,12-tetraazabicyclo [6.6.2]hexadecane Manganese(III) Hexafluorophosphate
Diaquo-5,12-dimethyl-1,5,8,12-tetraazabicyclo[6.6.2]hexadecane Manganese(II) Tetrafluoroborate
Dichloro-5,12-dimethyl-1,5,8,12 tetraazabicyclo[6.6.2] hexadecane Manganese(III) Hexafluorophosphate
Dichloro-5,12-diethyl-1,5,8,12-tetraazabicyclo[6.6.2]hexadecane Manganese(M) Hexafluorophosphate
Dichloro-5,12-di-n-butyl-1,5,8,12-tetraazabicyclo[6.6.2] hexadecane Manganese(II)
Dichloro-5,12-dibenzyl-1,5,8,12-tetraazabicyclo[6.6.2] hexadecane Manganese(II)
Dichloro-5-n-butyl-12-methyl-1,5,8,12-tetraaza-bicyclo [6.6.2]hexadecane Manganese(II)
Dichloro-5-n-octyl-12-methyl-1,5,8,12-tetraaza-bicyclo [6.6.2]hexadecane Manganese(II)

Dichloro-5-n-butyl-12-methyl-1,5,8,12-tetraaza-bicyclo [6.6.2]hexadecane Manganese(II).

Bleach Boosting Compounds may be used in the present invention and may comprise one or more bleach boosting compounds. Bleach boosting compounds provide increased bleaching effectiveness in lower temperature applications. The bleach boosters act in conjunction with conventional peroxygen bleaching sources to provide increased bleaching effectiveness. This is normally accomplished through in-situ formation of an active oxygen transfer agent such as a dioxirane, an oxaziridine, or an oxaziridinium. Alternatively, preformed dioxiranes, oxaziridines and oxaziridiniums may be used.

Among suitable bleach boosting compounds for use in the present invention are cationic imines, zwitterionic imines, anionic imines and/or polyionic imines having a net charge of from about +3 to about −3, and mixtures thereof. These imine bleach boosting compounds of the present invention include those of the general structure:

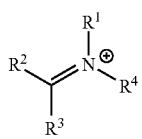

[I]

where $R^1$-$R^4$ may be a hydrogen or an unsubstituted or substituted radical selected from the group consisting of phenyl, aryl, heterocyclic ring, alkyl and cycloalkyl radicals.

Bleach boosting compounds may include zwitterionic bleach boosters, which are described in U.S. Pat. Nos. 5,576,282 and 5,718,614. Other bleach boosting compounds include cationic bleach boosters described in U.S. Pat. Nos. 5,360,569; 5,442,066; 5,478,357; 5,370,826; 5,482,515; and 5,550,256, as well as WO App. Nos. 95/13351; 95/13352; and 95/13353.

The bleach boosting compounds, when present, may be employed in conjunction with the peroxygen bleaching compound in the bleach activator systems of the present invention.

Dispersant aids/binders may be used in the present invention. These materials may be used to aid in distributing the bleach activator systems through out the entire core of the absorbent article while also aiding in keeping the peroxygen bleaching compound and bleach activator closely associated with one another. These dispersant aids may have low melting solids to enable mixing with the bleach activator materials and may be hydrophilic to provide sufficient wetting and activation of the peroxygen bleach compounds. Dispersant aids may include glucose, sorbitol, maltose, glucamine, sucrose, polyvinyl alcohol, starch, alkyl polyglycoside, sorbitan fatty ester, polyhydroxy fatty acid amides containing from about 1 to about 18 carbon atoms in their fatty acid moieties, and mixtures thereof. Dispersant aids may also include a polyethylene glycol polymer available from The Dow Chemical Company, Midland Mich. under the tradename Carbowax.

Additional odor control materials may be used in the present invention. These materials may be classified according to the type of odor the agent is intended to combat. Odors may be chemically classified as being acidic, basic, or neutral. Alternatively, the odor control agents may be categorized with respect to the mechanism by which the malodor detection is reduced or prevented. For example, odor control agents that chemically react with malodorous compounds or with compounds that produce malodorous degradation products thereby generating compounds lacking odor or having an odor acceptable to consumers may also be used. For instance, carbonates (e.g., sodium carbonate), bicarbonates (e.g., sodium bicarbonate), phosphates (e.g., sodium phosphate), sulphates (e.g., zinc and copper sulphates), carboxylic acids such as citric acid, lauric acid, boric acid, adipic acid and maleic acid, zinc salts of carboxylic acids such as zinc ricinoleate, transition metals, activated carbons, clays, zeolites, silicas, superabsorbent polymers, and starches may be used. Such odor control agents and systems are disclosed in EP-A-348 978; EP-A-510 619; WO 91/12029; WO 91/11977; WO 91/12030; WO 81/01643; and WO 96/06589.

Chelating agents may also be used and may include amino carboxylates such as ethylenediamine-tetracetate (described in U.S. Pat. No. 4,356,190), amino phosphonates such as ethylenediaminetetrakis (methylene-phosphonates), and polyfunctionallysubstituted aromatic chelating agents (described in U.S. Pat. No. 3,812,044).

Another suitable odor control agent that may be used in the present invention is a buffer system, such as citric acid and sodium bicarbonate, sodium phosphate and sorbic acid buffer systems. Also, buffer systems having a pH of from 7 to 10 (described in WO 94125077) may be used.

Ion exchange resins, such as those described in U.S. Pat. Nos. 4,289,513 and 3,340,875 may also be used as odor control agents, as well as hydrophobic porous polymers, including those described in WO2005/120594. Masking agents, such as perfumes, may also be used as odor control agents.

Preformed Peracids may be used in addition to the bleach activator systems of the present invention. The preformed peracid compound may include any convenient compound that is stable and that, under consumer use conditions, provides an effective amount of peracid or peracid anion. The preformed peracid compound may include percarboxylic acids and salts, percarbonic acids and salts, perimidic acids and salts, peroxymonosulfuric acids and salts, and mixtures thereof. Examples of these are described in U.S. Pat. No. 5,576,282.

One class of suitable organic peroxycarboxylic acids of the present invention may have the general formula:

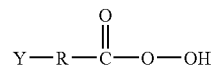

wherein R is an alkylene or substituted alkylene group containing from 1 to about 22 carbon atoms or a phenylene or substituted phenylene group, and Y is hydrogen, halogen, alkyl, aryl, —C(O)OH or —C(O)OOH.

Organic peroxyacids suitable for use in the present invention can contain either one or two peroxy groups and can be either aliphatic or aromatic. When the organic peroxycarboxylic acid is aliphatic, the unsubstituted peracid has the general formula:

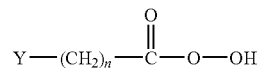

where Y can be, for example, H, $CH_3$, $CH_2Cl$, C(O)OH, or C(O)OOH; and n is an integer from 0 to 20. When the organic peroxycarboxylic acid is aromatic, the unsubstituted peracid has the general formula:

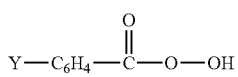

wherein Y can be, for example, hydrogen, alkyl, alkylhalogen, halogen, C(O)OH or C(O)OOH.

Monoperoxy acids useful herein include alkyl and aryl peroxyacids such as:
  (i) peroxybenzoic acid and ring-substituted peroxybenzoic acid, e.g., peroxy-a-naphthoic acid, monoperoxyphthalic acid (magnesium salt hexahydrate), and o-carboxybenzamidoperoxyhexanoic acid (sodium salt);
  (ii) aliphatic, substituted aliphatic and arylalkyl monoperoxy acids, e.g., peroxylauric acid, peroxystearic acid, N-nonanoylaminoperoxycaproic acid (NAPCA), N,N-(3-octylsuccinoyl)aminoperoxycaproic acid (SAPA) and N,N-phthaloylaminoperoxycaproic acid (PAP); and
  (iii) amidoperoxyacids, e.g., mononolylamide of either peroxysuccinic acid (NAPSA) or of peroxyadipic acid (NAPAA).

Diperoxyacids useful herein include alkyl diperoxyacids and aryldiperoxyacids, such as:
(i) 1,12-diperoxydodecanedioic acid;
(ii) 1,9-diperoxyazelaic acid;
(iii) diperoxybrassylic acid; diperoxysebacic acid and diperoxyisophthalic acid;
(iv) 2-decyldiperoxybutane-1,4-dioic acid; and
(v) 4,4'-sulfonylbisperoxybenzoic acid.

Such bleaching agents are disclosed in U.S. Pat. Nos. 4,483,781; 4,412,934; 4,634,551; and European Patent Application 0,133,354. Sources may also include 6-nonylamino-6-oxoperoxycaproic acid, described in U.S. Pat. No. 4,634,551. Persulfate compounds (including OXONE, manufactured commercially by E.I. DuPont de Nemours of Wilmington, Del.) can also be employed as a suitable source of peroxymonosulfuric acid. PAP is disclosed in, for example, U.S. Pat. Nos. 5,487,818; 5,310,934; 5,246,620; 5,279,757; and 5,132,431.

Bleach Activator System as a Co-Particle

The peroxygen bleaching compounds and bleach activator materials of the present invention can be incorporated into the absorbent articles by any means or in any form that allows in-situ generation of the peroxyacid. This could include the addition of the two materials added separately or as a pre-mixed solid to the absorbent article. For instance, the peroxygen bleaching compound and bleach activator may be delivered to the absorbent article as a co-particle composition through the use of a dispersant aid/binder material as disclosed herein or as disclosed in WO 2007/127641.

Bleach Activator System as a Multiple Particle Mixture

The peroxygen bleaching compound and bleach activator may also be delivered to the absorbent article as a mixture of particles. For instance, the bleach activator may be in the form of an extrudate as disclosed in U.S. Pat. Nos. 4,486,327 and 6,617,300 and then mixed with a peroxygen bleaching compound to provide a multiple particle bleach activator system. Additionally, in another embodiment of the present invention, the bleach activator may be coated onto a core particle through the use of suitable binders and coating materials as disclosed in WO 2005/080542 and then mixed with an appropriate amount of peroxygen bleaching compound to provide a multiple particle bleach activator system.

Suitable core materials used to make the bleach activator particle include, but are not limited to, ingredients such as sodium sulfate, sodium carbonate and sodium phosphate, as well as composite detergent ingredient compositions made by processes such as spray-drying, agglomeration, compaction, and/or extrusion processes. Examples of such composite compositions include particles/granules comprising detergent builder, surfactant and, optionally, polymer ingredients. Suitable core materials may have a particle size that is comparable to the peroxygen bleach compound to provide proper mixing between the peroxygen bleach compound and the bleach activator particle and may have a particle size that will range from about 200-1300 µm and may have an average particle size from about 500-1000 µm. While suitable cores, such as detergent particles/granules, are typically made as an intermediate within a detergent production facility, suitable cores and core raw materials can be obtained from FMC Corporation of Philadelphia, Pa., U.S.A.; Jost Chemicals of St. Louis, Mo., U.S.A.; General Chemical Corporation of Parsippany, N.J., U.S.A; and Mallinckrodt Baker of Phillipsburg, N.J., USA. Additionally, superabsorbent polymers may also be used as suitable core components and can be obtained from BASF of Ludwigshafen, Germany; Nippon Shokubai of Osaka, Japan; and Evonik Degussa of Düsseldorf, Germany. Further, suitable core materials can be chosen from polymeric particles, inorganic salts, clays, mica, starches, sugars, zeolites, silicon dioxide and inorganic coordination complexes.

Suitable binder materials used to make the bleach activator particle include materials selected from the group consisting of polymers, surfactants, solvents, and mixtures thereof. Examples of polymers include sodium polyacrylate, acrylic-maleic co-polymers, polyethylene glycol, polyvinyl acetate, polyvinyl pyrrolidone, cellulose ethers, and hydroxypropyl cellulose. Examples of surfactants include anionic, cationic, zwitterionic and nonionic surfactants. Examples of solvents include water, alcohols, linear alcohols, branched alcohols, and fatty alcohols. Suitable binders can be obtained from BASF of Ludwigshafen, Germany; Dow Chemical Company of Midland, Mich., U.S.A.; Hercules Incorporated of Wilmington, Del., U.S.A.; Shell Chemical LP of Houston, Tex., U.S.A.; Procter & Gamble Chemicals of Cincinnati, Ohio, U.S.A.; and Rohm and Hass Company of Philadelphia, Pa., U.S.A.

Suitable solid coating aids used to make the bleach activator particle include materials selected from the group consisting of acetates, sulfates, carbonates, borates, phosphates, and mixtures thereof. Examples of acetates include magnesium acetate, $Mg(CH_3COO)_2$; and sodium acetate, $NaCH_3COO$. Examples of sulfates include magnesium sulfate, $MgSO_4$; and sodium sulfate, $Na_2SO_4$. Examples of carbonates include sodium carbonate, $Na_2CO_3$; potassium carbonate, $K_2CO_3$. Examples of borates include sodium borate, $Na_2B_4O_7$. Examples of phosphates include sodium phosphate dibasic, $Na_2HPO_4$; and sodium tripolyphosphate, $Na_5P_3OIO$. Such coating aids may be introduced to the coating process as substantially anhydrous salts. While not being bound by theory, it is believed that their conversion to stable hydrate phases provides a mechanism for the removal of binder moisture and enables processing without the requirement of a drying step. Suitable solid coating aids can be obtained from PQ Corporation of Valley Forge, Pa., U.S.A.; FMC Corporation of Philadelphia, Pa., U.S.A.; and Mallinckrodt Baker, Inc. of Phillipsburg, N.J., U.S.A.

In addition, the bleach activator particle may also optionally comprise dyes and pigments for the purpose of conveying a signal to the caregiver. The signal may communicate the presence of the bleach activator particle. Non-limiting examples of dyes and pigments include organic and inorganic pigments, aqueous and other solvent-soluble dyes. Such dyes and pigments can be obtained from Ciba Specialty Chemicals Corporation of Newport, Del., U.S.A.; Clariant Corporation of Charlotte, N.C., U.S.A.; and Milliken Chemical Company of Spartanburg, S.C., U.S.A. Suitable equipment for performing the particle making processes disclosed herein includes paddle mixers, ploughshare mixers, ribbon blenders, vertical axis granulators, and drum mixers, both in batch and, where available, in continuous process configurations. Such equipment can be obtained from Lodige GmbH (Paderborn, Germany), Littleford Day, Inc. (Florence, Ky., U.S.A.), Forberg AS (Larvik, Norway), Glatt Ingenieurtechnik GmbH (Weimar, Germany). Further, the bleach activator particle may also optionally be dried to remove any moisture prior to being mixed with the peroxygen bleach compound of the multiple particle bleach activator system.

In one aspect of the present invention, said bleach activator particle comprises, based on total particle weight, no more than about 50 weight percent of any bleach activator, no more than about 20 weight percent of any bleach activator active, no more than about 10 weight percent of any bleach activator active, or no more than about 5 weight percent of any bleach activator active.

The multiple particle bleach activator system of the present invention may be formed by mixing the peroxygen bleach compound with the bleach activator particle. Suitable equipment for performing the mixing process includes, but is not limited to paddle mixers, such as a Forberg mixer and rotating drum mixers.

Absorbent Article

The disposable absorbent articles of the present invention may comprise a topsheet having a garment facing surface and a body facing surface, a backsheet having a garment facing surface and a body facing surface, and an absorbent core disposed between said body facing surface of the backsheet and the garment facing surface of the topsheet.

In certain embodiments, the absorbent articles may take the form of a diaper, a pant product, an adult incontinence product, or a feminine hygiene product, e.g., a sanitary napkin or panty liner. Given these various product forms, additional components may also exist within the disposable absorbent article. Such components may be selected from the group consisting of an outer cover, side panels, a cuff, an elastic feature, a wing, a fastening system, and combinations thereof.

Absorbent Core

The articles of the present disclosure may additionally comprise one or more absorbent cores. The absorbent core is at least partially disposed between the topsheet and the backsheet and may take on any size or shape that is compatible with the disposable absorbent article. Exemplary absorbent structures for use as the absorbent core of the present invention that have achieved wide acceptance and commercial success are described in U.S. Pat. Nos. 4,610,678; 4,673,402; 4,888,231; and 4,834,735; and U.S. Pub. Nos. 2005-0273071, 2005-0171499, 2007-0191806, 2004-0162538, and 2005-0095942. The absorbent core may further comprise the dual core system containing an acquisition/distribution core of chemically stiffened fibers positioned over an absorbent storage core as detailed in U.S. Pat. Nos. 5,234,423 and 5,147,345.

As discussed herein "absorbent gelling materials" and "superabsorbent polymers" are those materials that, upon contact with aqueous fluids, such as bodily fluids, imbibes such fluids and form hydrogels. These absorbent gelling materials are typically capable of absorbing large quantities of aqueous bodily fluids, and further capable of retaining such absorbed fluids under moderate pressures. These absorbent gelling materials are typically in the form of discrete, nonfibrous particles. Other forms, such as fibers, foams, sheets, strips, or other macrostructures, are also suitable for use herein. Suitable absorbent gelling materials in the form of open cell foams may include those disclosed in U.S. Pat. Nos. 3,563,243; 4,554,297; 4,740,520; and 5,260,345.

In certain embodiments of the present disclosure, the absorbent article may also include a sublayer disposed between the topsheet and the backsheet. The sublayer may have a body facing surface and a garment facing surface and may be any material or structure capable of accepting, storing or immobilizing bodily exudates. Thus, the sublayer may include a single material or a number of materials operatively associated with each other. Further, the sublayer may be integral with another element of the absorbent article or may be one or more separate elements joined directly or indirectly with one or more elements of the article. Further, the sublayer may include a structure that is separate from the core or may include or be part of at least a portion of the core.

Additionally, suitable absorbent cores may contain reduced amounts of cellulosic airfelt material. For instance, such cores may comprise less than about 40%, 30%, 20%, 10%, 5%, or even 1%. Such a core comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; 6,790,798; and U.S. Patent Publications 2004/0158212A1 and 2004/0097895A1; and U.S. application Ser. Nos. 10/758,375 and 10/758,138.

In further embodiments, the articles according to the present disclosure may further comprise a wetness sensation member. This member may be disposed in various locations within the article. For instance, the wetness sensation member may be disposed on the topsheet. The member may comprise a permeable layer and an impermeable layer, wherein urine passes through the permeable layer and not through the impermeable layer such that a wearer is made of aware of the fact that urination has occurred as a result of the "wet" feeling. Suitable members are detailed in U.S. Pat. No. 6,627,786.

Bleach activator systems of the present invention may be incorporated into the absorbent articles described in U.S. Pub. Nos. 2005-0273071, 2005-0171499, 2007-0191806, 2004-0162538, and 2005-0095942. Further, bleach activator systems of the present invention may be placed in or on the different absorbent article components described above, including an absorbent core, an acquisition system, barrier leg cuffs, a backsheet, and/or a topsheet.

Further, they may be incorporated into lotions applied to the topsheet. These lotions may be hydrophilic or hydrophobic. For instance bleach activator systems may be suspended in the lotion.

The effectiveness of the odor control system comprising a bleach activator system of the present invention can be demonstrated by determining the percent reduction in the concentration of common odorant molecules in the headspace surrounding a urine loaded diaper comprising said bleach activator system. The headspace surrounding a urine loaded aged diaper can be found to contain many odiferous compounds; and Headspace Gas Chromatography/Mass Spectrometry analysis can be used to evaluate changes in the presence and concentration of molecules in said headspace. In this test, a given volume of headspace is collected from an aged urine loaded diaper onto a Tenax trap that is then attached to an Agilent Technologies 6890 Gas Chromatograph equipped with a HP 5973 Mass Spectrometry detector and a Gerstel ODP Sniffport. A control diaper (blank) containing no odor control material is analyzed along with a diaper comprising sodium percarbonate alone (See Example 5) and a diaper comprising the multiple particle bleach activator odor control system (See Example 4) of the present invention. Dimethyl disulfide and 4-Heptanone are chosen as the odorant molecules for the analysis as they are commonly found in the headspace associated with bodily waste products such as urine, menses, and feces. Tables 1 & 2 display the results of the Headspace GC/MS analysis as demonstrated by the GC/MS Total ion Chromatogram Abundance for dimethyl disulfide and 4-heptanone, respectively. The total ion Chromatogram Abundance is representative of the molecular concentration of the odorant molecules in the headspace and the control diaper represents the maximum concentration of odorant molecules present under the test conditions because it contained no odor control system.

The diaper comprising the sodium percarbonate demonstrates an 18% reduction in the amount of dimethyl disulfide and a 32% reduction in the amount of 4-heptanone in the headspace as compared to the control diaper. These results are in sharp contrast to the diaper comprising a multiple particle bleach activator odor control system of the present invention that more effectively reduces the concentration of these odorants in the headspace. This diaper demonstrates a 77% reduction in dimethyl disulfide and a 56% reduction of 4-heptanone in the headspace as compared to the control diaper. The ability of multiple particle bleach activator odor control system to significantly reduce the concentration of odorant molecules derived from urine may be advantageous in certain embodiments of the present invention.

TABLE 1

Removal of Dimethyldisulfide

| Test Material | GC/MS Total Ion Chromatogram Abundance | Approximate reduction as compared to blank |
|---|---|---|
| Control (Blank) | 6742 | — |
| Bleach Activator system (Example 4) | 1513 | 77% |
| Sodium Percarbonate (Example 5) | 5542 | 18% |

TABLE 2

Removal of 4-Heptanone

| Test Material | GC/MS Total Ion Chromatogram Abundance | Approximate reduction as compared to blank |
|---|---|---|
| Control (Blank) | 3317 | — |
| Bleach Activator system (Example 4) | 1455 | 56% |
| Sodium Percarbonate (Example 5) | 2271 | 32% |

Test Methods

High Performance Liquid Chromatography (HPLC) Test for Nonanoyloxybenzenesulfonate Bleach Activator A suitable test method for the quantification of Nonanoyloxybenzenesulfonate (NOBS) either from particles coated with NOBS or an absorbent article containing such particles, is by HPLC with UV detection. Analysis is conducted on an Waters 2695 liquid chromatograph solvent delivery system, in-line degasser, autosampler, column heater (set at 35° C.) and a photodiode array detector and supported by Empower software for instrument control, data collection and processing. Chromatography is performed on a Dionex Acclaim® Polar Advantage reverse phase column (C16 3 micron 150× 4.6 mm Part #061318) using a binary gradient, at 1 mL/minute flow rate, with UV detection at 220 nm. Extraction of an absorbent article is described below. The extract is filtered through a 0.45 micron PTFE Acrodisc CR filter before 5 µL is injected for analysis.

Reagents and Solutions:
Extraction Solvent: Denatured (95%) Ethanol: Glacial Acetic Acid:Water (40:20:40 by weight)
Bleach activator standard: Nonanoyloxybenzenesulfonate (NOBS) powder of known activity
HPLC Eluent A—Aqueous 0.01 M Ammonium Dihydrogen Orthophosphate (HPLC grade)
HPLC Eluent B—70:30 HPLC Grade Acetonitrile:Water (HPLC grade)
HPLC Gradient Elution Profile

| Time (min) | Eluent A (%) | Eluent B (%) | Flow (mL/min) |
|---|---|---|---|
| 0 | 70 | 30 | 1.00 |
| 10 | 5 | 95 | 1.00 |
| 12.5 | 5 | 95 | 1.00 |
| 13 | 70 | 30 | 1.00 |
| 18 | 70 | 30 | 1.00 |

Preparation of Calibration Standards:
All standards are prepared using Class A volumetric glassware. First, approximately 100 mg of the NOBS primary standard is accurately weighed and transferred to a 100 mL volumetric flask, brought to volume with the extraction solvent, and mixed thoroughly. Next, calibration standards of approximately 10, 20, 40 and 80 mg/L are prepared by pipeting 1.0, 2.0, 4.0 and 8.0 mL of the stock solution, each into a separate 100 mL volumetric flask, brought to volume with the extraction solvent, and mixed thoroughly. If needed, additional calibration standards can be prepared to assure that the concentration of the NOBS falls within the span of the calibration curve.

HPLC Analyses:
5 µL of each calibration standard and sample is injected. The integrated peak areas for the calibration standards are used to prepare a calibration curve of Response (peak area) verses Concentration from which the concentration of NOBS can be calculated. Report results to +0.1 mg/mL. This value can be used to calculate the weight % of NOBS on a particle or the total NOBS extracted from an absorbent article.

weight %=measured NOBS concentration (mg/L)* dissolution volume (L)/particle mass (mg)*100 mg/diaper=measured NOBS concentration (mg/L)* extraction volume (L)/diaper

Results are reported to ±0.1% or +0.1 mg/diaper.

Reflectoquant Peroxide Test

Equipment:
Reflectoquant Meter; RQflex 10, available from EMD Chemicals
Peroxide Test Strips; stock number 16974; measuring 0.2-20.0 mg/mL concentration range Method:

For the peroxide measurement, the Reflectoquant is set-up to use method 643 for the analysis. At a given time period after sample dissolution, the peroxide test strip is dipped directly into a stirred solution containing peroxide and held there for 2 seconds and then removed and shaken to get rid of excess solution. At the same time the test strip is placed in the solution, the 15 second timer on the Reflectoquant Meter is activated. After removing the excess solution from the test strip, it is inserted into the machine and at the end of the 15 second timer, the reflectoquant analyzes the test strip and displays the concentration of peroxide (ppm).

Diaper Extraction Test

Representative diaper is prepared for extraction by carefully cutting the diaper into small pieces (approximately 2-4 square inches) over a tray to catch any materials lost from core. The diaper material is placed in a 16 oz high density wide mouth jar (available from VWR International; Catalog #15900-106) and treated with 200 mL of 40:20:40 by weight mix of Denatured Ethanol (95%): Glacial Acetic Acid: Dionized Water extraction solvent. The lid (equipped with Plastisol liner; available from VWR International; Catalog #16198-905) is placed tightly on the jar to ensure no solution is lost and the jar is placed on a US Stoneware roller type jar mill (available from VWR international; Catalog #48900-000) on a setting of 10 for 30 minutes. The jars are placed inside a disposable nitrile glove (such as those available from VWR International; Catalog #40101-348) to help maintain proper contact with the rollers of the mill and ensure proper mixing. The extraction solvent is collected by squeezing the diaper material within the jar and pouring the resulting liquid into a collection container. The extraction solvent is placed in a refrigerator until analysis and should be conducted within 3 days.

Gas Chromatography/Mass Spectrometry (GC/MS) Headspace Test

GC/MS Headspace testing is conducted using an Agilent 6890 Gas Chromatograph equipped with a BP 5973 Mass Spectrometer and Programmed Temperature Vaporization (PTV) injector, (Agilent, Santa Clara, Calif.) and a Gerstel ODP Sniffport (Linthicum, Md.). The column oven and PTV injector are plumbed for liquid nitrogen cooling. An Agilent DB-5-MS, 60 m×0.32 mm i.d. column with a 1 μm film thickness is used for the separation with the column effluent split 50:50 to the sniffport and MS. A standard PTV liner containing 25 mg of Tenax TA absorbent packed between 2 plugs of silanized glass wool is used for injection. The auxiliary flow of the GC is plumbed to connect to the 1/16" fitting of the desorption tube, and the auxiliary heater is configured to power a syringe heater which is used to heat the desorption tube once its needle is placed into the PTV injector. Temperatures for the MS are set to 280° C. for the transfer line, 150° C. for the quadrupole, and 230° C. for the source. The MS is configured for EI scan mode, scanning from 45-350 m/z.

Figure 4:
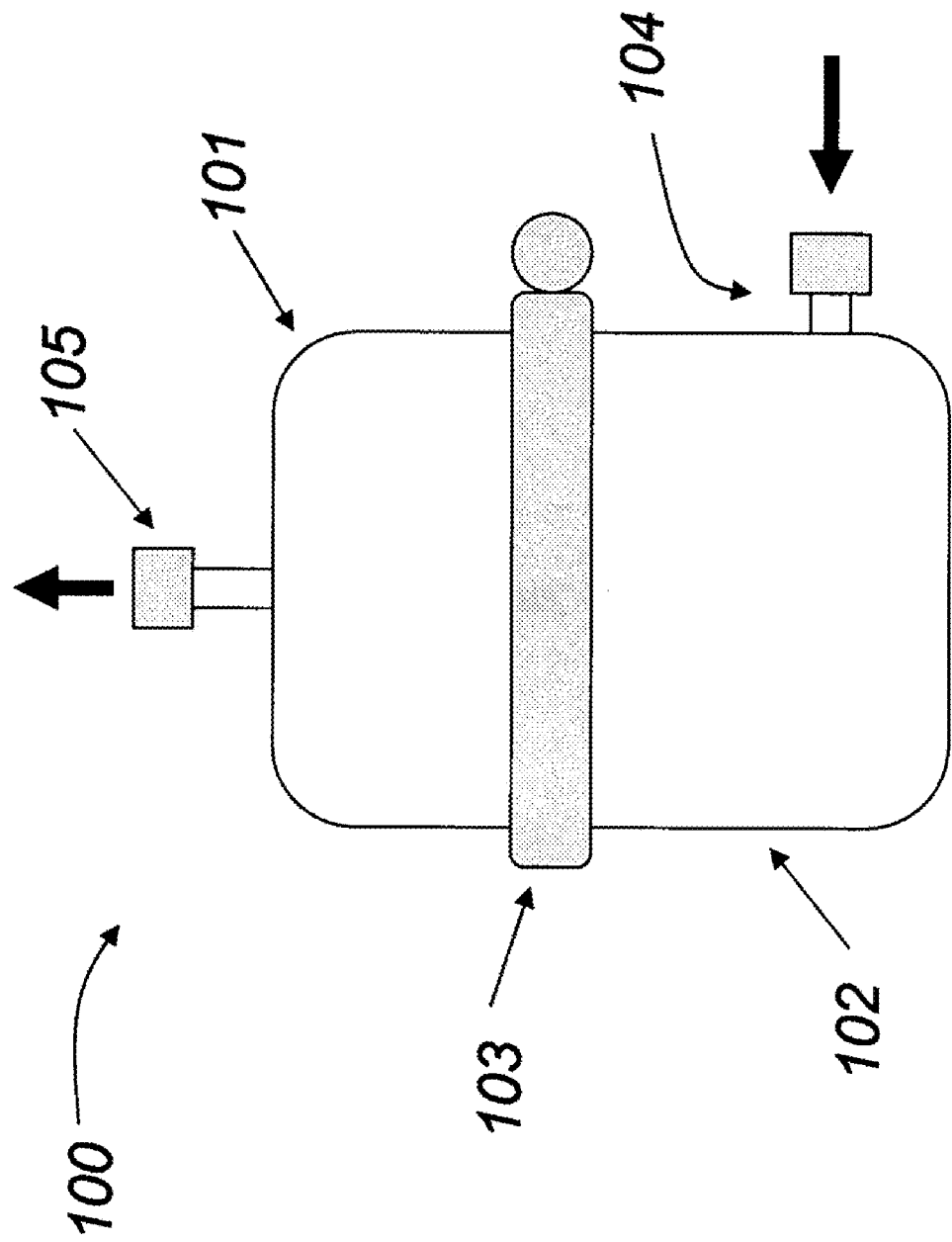
FIG. 4 is a side view of a headspace sample vessel.

Volatiles are collected on a GLT Silco™ coated stainless steel desorption tube (Scientific Instruments Services, Ringoes, N.J.) 100 mm×4 mm i.d. containing 125 mg of Tenax TA absorbent packed between 2 plugs of silanized glass wool. The desorption tube is sealed with a 1/16" female fitting at one end and a 35 mm syringe needle at the other. As illustrated in FIG. 4, a glass 1.5 liter headspace vessel 100 consist of a top 101 which forms a leak-free seal to the bottom 102 using an o-ring and ring clamp 103. The bottom has an inlet port 104 where the helium purge is connected. The top 101 has an outlet port 105 with a fitting for syringe needle of the desorption tube.

Fresh male urine is collected into sterile specimen cups (VWR International) from about 10 subjects using the first urination of the day and pooled together to provide a representative urine sample. The sample absorbent article is loaded with 200 mL of the male pooled urine at the acquisition point of the article and placed into the headspace vessel which is sealed and allowed to age at room temperature for 16 hours. After aging, a preconditioned, packed, desorption tube is attached to the outlet of the headspace vessel via the syringe needle and the inlet is attached to a regulated helium supply. The flow is preset to deliver a 40 mL/min. flow of helium which sweeps through the vessel and desorption tube (which traps the volatiles swept from the vessel) for 30 minutes yielding a 1.2 liter gas sampling of the headspace.

After collection, the desorption tube is removed from the headspace vessel, and the needle inserted into the PTV injector. The syringe heater is placed around the desorption tube and the auxiliary helium flow connected. The initial temperature of the syringe heater and PTV is 30° C.; the oven temperature is 50° C.; and the auxiliary helium pressure is 8 psi. The syringe heater is ballistically heated to a final temperature of 300° C. for a total of 20 minutes. The desorption tube is removed and the PTV is programmed for a splitless injection: 20 psi helium flow, purge flow 7.0 mL/min., purge time 5.0 minutes, total flow of 12.4 ml/min, and ballistically heated from 30 to 300° C. starting at 0.1 minutes.

GC oven temperature programming is held at 50° C. for 2 minutes, then heated at a rate of 6.0° C./min to 285° C. and held at that temperature for 10 minutes. Total Ion Chromatograms (TIC) for the mass range of 45-350 m/z is collected after an initial 2 minute solvent delay. Concurrently, olfactory sniffport evaluation is conducted by the operator recording the presence, intensity and description of the odors perceived for each sample tested. The integrated peak area of the response of odor specific components (for example dimethyl disulfide and 4-heptanone) is obtained from the total ion chromatogram and is used in determining the percent reduction of the odor specific components as compared to a control diaper with no odor control material present (blank).

EXAMPLES

The following examples are given solely for the purposes of illustration and are not to be construed as limitations of the present disclosure.

Example 1

Process for Making a Bleach Activator Co-Particle

This process is practiced in a food processor (mixer), with a vertical axis-driven impeller having a radial sweep of 8.0 cm. To a 14-speed Osterizer blender is added Sodium Nonanoyloxybenzene sulfonate extrudate (NOBS, Future Fuels Chemical Company) which is ground to a fine powder. In a batch wise process, 200.0 g Sodium Percarbonate (OCI Chemical Corp, Decatur, Ala. under the tradename Provox C) and 10.0 g ground NOBS are combined and blended together in an Osterizer blender for 30 seconds. Next, the Sodium Percarbonate/NOBS mixture (205.0 g) is vigorously mixed with 205.0 g of molten PEG 4600 in a preheated beaker (80° C.) for about 30 seconds. The viscous molten material is then poured onto a strip of aluminum foil (or may alternatively be poured into a plastic Ziploc bag) and, using spatula, spread out into a thin layer. The ends of the aluminum foil are folded over (or the Ziploc bag is closed) to seal the material inside and the packet is placed into a freezer for about 15 minutes until completely solid. The packet is removed from freezer, allowed to equilibrate to room temperature while remaining sealed, and then the material is removed and broken into small pieces prior to being placed back in the Osterizer blender and ground. This procedure is carried out for 16 batches which are combined prior to sieving. The collected material is sieved through an 850 μm mesh screen and onto a 250 μm. Anything collected on the 850 μm mesh screen is reground and sieved again. This process produces 3400 g of material through 850 μm mesh screen and onto a 250 μm mesh screen (target); 2175 g of material through a 250 μm mesh screen (fines); and 624 g of material left on a 850 μm mesh screen (overs).

Example 2

Process for Making a Bleach Activator Particle

This process is practiced in a Bella XL-32 paddle mixer (Dynamic Air, St. Paul Minn.). This example describes a process to making a bleach activator particle with a 10% loading level of bleach activator, such as Nonanoyloxybenzene sulfonate. Twenty-four kilograms of the core anhydrous sodium sulfate material (Mallinckrodt Baker, Product 8024, 10-60 Mesh) is loaded into the mixer. The mixer is started, using a paddle tip speed of 2.1 m/s. At an elapsed time of 10 seconds, 1.2 kg of binder (Acusol 445N, Rolm and Haas, diluted with water to a solids concentration of about 36%) is begun to be added to the mixer, continuing at a rate of 400 g/minute via top-spray atomization on the center fluidized zone. At an elapsed time of 30 seconds, 3.0 kg of bleach activator powder (Nonanoyloxybenzene sulfonate powder, Future Fuels Chemical Company) is begun to be added to the mixer at a rate of 1.5 kg/minute. At an elapsed time of 78 seconds, 1.80 kg of micronized anhydrous magnesium sulfate powder is begun to be added to the mixer at a rate of 1.0 kg/minute. Mixing is continued until a total elapsed time of 420 s, at which time the mixer is stopped and the batch discharged. The resulting batch is sieved through 1150 um and onto 250 um to provide 27.8 kg of bleach activator particles. To determine the loading level of bleach activator on the core particle, dissolve 0.100 g of the bleach activator particle in 200 mL of 40:20:40 by weight mix of Denatured Ethanol (95%): Glacial Acetic Acid: Deionized Water and conduct the Liquid Chromatography (LC) Test for Bleach Activator Loading Level to determine the concentration and weight of bleach activator dissolved in the solution. The loading level of bleach activator on the core particle is determined by dividing the weight of bleach activator in solution by the total weight of particle dissolved in the test solution, and multiplying by 100. The loading level of Nonanoyloxybenzene sulfonate bleach activator on this particle is found to be 10.2%.

Example 3

Process for Making a Multiple Particle Bleach Activator System

To 20.0 grams of Sodium Percarbonate (ECOX-C, Kemira Kemi AB) is added 10.0 grams of bleach activator particle as described in Example 2 and the material is gently mixed. To determine the relative mole ratio of peroxide:bleach activator in the multiple particle bleach activator system, the weight and number of moles of peroxide and bleach activator in a given weight of sample needs to be determined. For peroxide, 0.300 g of the multiple particle bleach activator system is dissolved in 4 L of distilled water and after 30 minutes, the concentration of peroxide is determined using the Reflectoquant Peroxide Test. The analysis is performed in triplicate and the average peroxide concentration determined (Measured—15.53 mg/L; Theoretical—15.43). The weight of peroxide in the solution is determined by multiplying the average peroxide concentration by the volume of water (4 L) the bleach activator system is dissolved in. For analysis of the bleach activator, 0.300 g of the multiple particle bleach activator system is dissolved in 200 mL of 40:20:40 by weight mix of Denatured Ethanol (95%): Glacial Acetic Acid: Deionized Water and the concentration of Nonanoyloxybenzene sulfonate (NOBS) determined using the Liquid Chromatography (LC) Test for Bleach Activator Loading Level. The analysis is performed in triplicate and the average NOBS concentration determined (Measured—51.01 ppm; Theoretical—50 ppm). The weight of nonanoyloxybenzene sulfonate (NOBS) is determined by multiplying the average NOBS concentration by the volume of solvent (0.2 L) the bleach activator system is dissolved in. The mole ratio of the hydrogen peroxide (delivered from the peroxygen source) to the bleach activator is 59.3:1.

Example 4

Absorbent Article Comprising Bleach Activator System

The multiple particle bleach activator system from Example 3 is incorporated into an unscented European Size 4 Baby Dry diaper, distributed by The Procter & Gamble Company, Cincinnati, Ohio. The diaper weighs from about 33.5 g to about 35 g. Said material is incorporated by first opening up the front end seam of the diaper by freezing the area with cold spray and carefully pulling the topsheet away from the backsheet to fracture the glue bond. To the opened end seam of the diaper, 0.300 g of powder from Example 5 is added directly into the core such that the material is intermixed with absorbent gelling material and air felt (i.e., cellulosic fibers). The end seam is re-secured by placing 0.006 gsi glue sheet (Bostik 2031) between the topsheet and backsheet, followed by treatment with a roller. The closed diaper is gently shaken once to more evenly distribute the odor control powder within the core.

The amount of bleach activator present in the diaper can be determine by conducting the diaper extraction test followed by performing the Liquid Chromatography (LC) Test for Bleach Activator Loading Level analysis on the extracted liquid. The amount of Nonanoyloxybenzene sulfonate (NOBS) determined to be in the diaper is 10.3 mg.

Example 5

Comparative Example

Sodium percarbonate is incorporated into an unscented European Size 4 Baby Dry diaper, distributed by The Procter & Gamble Company, Cincinnati, Ohio. The diaper weighs from about 33.5 g to about 35 g. Said material is incorporated by first opening up the front end seam of the diaper by freezing the area with cold spray and carefully pulling the topsheet away from the backsheet to fracture the glue bond. To the opened end seam of the diaper, 0.200 g of sodium percarbonate (ECOX-C, Kemira Kemi AB) is added directly into the core such that the material is intermixed with absorbent gelling material and air felt (i.e., cellulosic fibers).

The end seam is re-secured by placing 0.006 gsi glue sheet (Bostik 2031) between the topsheet and backsheet, followed by treatment with a roller. The closed diaper is gently shaken once to more evenly distribute the odor control powder within the core.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be apparent to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
    a topsheet;
    a backsheet;
    an absorbent core between the topsheet and backsheet;
    an odor control system in solid form, the odor control system comprising:
        a) a source of hydrogen peroxide; and
        b) a bleach activator capable of reacting with hydrogen peroxide to form a peracid.

2. The absorbent article of claim 1, wherein the source of hydrogen peroxide is selected from the group consisting of sodium percarbonate, sodium perborate, and combinations thereof.

3. The absorbent article of claim 1, wherein the bleach activator is selected from the group consisting of tetraacetyl ethylene diamine (TAED), benzoylcaprolactam (BzCL), 4-nitrobenzoylcaprolactam, 3-chlorobenzoyl-caprolactam, benzoyloxybenzenesulphonate (BOBS), nonanoyloxybenzenesulphonate (NOBS), phenyl benzoate (PhBz), decanoyloxybenzenesulphonate ($C_{10}$-OBS), benzoylvalerolactam (BZVL), octanoyloxybenzenesulphonate ($C_8$-OBS), 4-[N-(nonaoyl)amino hexanoyloxy]-benzene sulfonate sodium salt (NACA-OBS), dodecanoyloxybenzenesulphonate (LOBS or $C_{12}$-OBS), 10-undecenoyloxybenzenesulfonate (UDOBS or $C_{11}$-OBS with unsaturation in the 10 position), and decanoyloxybenzoic acid (DOBA) perhydrolyzable esters, and mixtures thereof.

4. The absorbent article of claim 1, wherein a leaving group (L) of the bleach activator is selected from the group consisting of oxybenzenesulfonate (OBS), oxybenzoic acid (OBA), and valerolactam (VL).

5. The absorbent article of claim 1, wherein the bleach activator is sodium nonanoyloxybenzenesulfonate (NOBS).

6. The absorbent article of claim 1, wherein the mole ratio of the hydrogen peroxide (neat or as delivered from the peroxygen source) to the bleach activator in the present invention ranges from at about 100:1 to about 1:1.

7. The absorbent article of claim 1, wherein the bleach activator is present at a level of from about 0.005 g to about 0.2 g.

8. The absorbent article of claim 1, wherein the bleach activator is present at a level of from about 0.001 g to about 0.05 g.

9. The absorbent article of claim 1, wherein the bleach activator is present at a level of from about 0.005 g to about 1.0 g.

10. The absorbent article of claim 1, wherein the bleach activator is present at a level of from about 0.01 g to about 0.05 g.

11. The absorbent article of claim 1, wherein the source of hydrogen peroxide and bleach activator is in the form of a co-particle.

12. The absorbent article of claim 1, further comprising an agent selected from the group consisting of an organic peroxide, a diacyl peroxide, a metal containing bleach catalyst, a bleach boosting compound, a preformed peracid, and mixtures thereof.

13. The absorbent article of claim 1, further comprising a perfume raw material.

14. The absorbent article of claim 13, further comprising an agent selected from the group consisting of absorbing gelling materials, silicas, zeolites, carbons, starches, chelating agents, pH buffered materials, cyclodextrine and derivatives thereof, chitin, kieselguhr, clays, ion exchange resins, hydrophobic porous polymers, carbonates, bicarbonates, phosphates, sulphates, carboxylic acids, zinc salts, transition metals and combination thereof.

15. The absorbent article of claim 1, wherein the source of hydrogen peroxide and the bleach activator are provided within the absorbent article such that they do not come in contact with a body-facing surface of the topsheet.

16. The absorbent article of claim 1, wherein the odor control system is disposed in the core, and wherein a preformed peracid is disposed in the core.

17. The absorbent article of claim 1, wherein the source of hydrogen peroxide and bleach activator are in the form of a multiple particle mixture.

18. The absorbent article of claim 17, wherein the bleach activator particle comprises, based on total particle weight, no more than 20 weight percent of any bleach activator active.

19. The absorbent article of claim 1, further comprising an agent selected from the group consisting of absorbing gelling materials, silicas, zeolites, carbons, starches, chelating agents, pH buffered materials, cyclodextrine and derivatives thereof, chitin, kieselguhr, clays, ion exchange resins, hydrophobic porous polymers, carbonates, bicarbonates, phosphates, sulphates, carboxylic acids, zinc salts, transition metals and combinations thereof.

20. An absorbent article comprising:
    a topsheet;
    a backsheet;
    an absorbent core between the topsheet and backsheet;
    an odor control system in solid form, the odor control system comprising:
        a) a peroxygen bleaching compound; and
        b) a bleach activator capable of reacting with hydrogen peroxide to form a peracid.

* * * * *